United States Patent [19]

Kudo et al.

[11] Patent Number: 5,101,024

[45] Date of Patent: Mar. 31, 1992

[54] HUMAN IMMUNOGLOBULIN AND ENHANCER GENE FRAGMENTS

[75] Inventors: Akira Kudo, Saga; Satoshi Nakamura; Yoshihiko Sumi, both of Hino; Yataro Ichikawa, Tokorozawa; Takeshi Watanabe, Saga, all of Japan

[73] Assignee: Teijin Limited, Osaka, Japan

[21] Appl. No.: 326,417

[22] Filed: Mar. 21, 1989

Related U.S. Application Data

[63] Continuation of Ser. No. 668,999, Nov. 5, 1984, abandoned.

[30] Foreign Application Priority Data

Nov. 8, 1983 [JP] Japan ................................ 58-208383
Dec. 6, 1983 [JP] Japan ................................ 58-229037
Jun. 4, 1984 [JP] Japan ................................ 59-113047
Jun. 5, 1984 [JP] Japan ................................ 59-113834

[51] Int. Cl.$^5$ ................ C12N 15/13; A61K 39/00; C07H 17/00
[52] U.S. Cl. .......................... 536/27; 435/70.21; 435/172.3; 435/320.1; 435/972; 436/512; 424/85.8; 935/15; 935/3; 935/33
[58] Field of Search ................ 435/172.3; 935/15, 36, 935/39; 536/27

[56] References Cited

U.S. PATENT DOCUMENTS 4,663,281 5/1987 Gillies et al. .................. 435/69.1

FOREIGN PATENT DOCUMENTS 0102634 3/1984 European Pat. Off. .

OTHER PUBLICATIONS

Gillies et al., Cell 33: 717–728, 1983 (Jul.).
Banerji et al. Cell 33: 729–740, 1983 (Jul.).
Maniatis et al, In Molecular Cloning: A Laboratory Manual, Cold Spring Harbor Labs. 1982, pp. 3–5, 24–27 and 31.
Rabbitts et al., Nature 306: , 806–809, 1983 (Dec.).
Hayday et al., Nature 307: 334–340, 1984 (Jan.).
Hieter et al., "Chem. Abst." 94 Col. 81895m (1981).
Siebenlist et al., "Nature", 294 631–635 (1981).
Ellison et al., "Nucleic Acids Research", 10(13), 4071–4079 (1982).

Primary Examiner—John Doll
Assistant Examiner—T. Michael Nisbet
Attorney, Agent, or Firm—Wenderoth, Lind & Ponack

[57] ABSTRACT

The present invention provides an enhancer DNA segment, a gene fragment having (a) the enhancer DNA segment and (b) a structural gene such as human D, V and J gene, and a promoter. A hybrid DNA (1) having a phage DNA fragment from Charon 4A phage vector and human DNA fragments, a Charon 4A phage containing the hybrid DNA (1), a hybrid DNA (2) having a PBR322 fragment and human DNA fragment, a transformant of E. coli C600 strain transformed with the hybrid DNA (2), plasmid pSV2-H1G1 obtained by inserting a human DNA fragment into a vector pSV-2gpt, a transformant of E. coli MC 1000 strain transformed with the plasmid pSV2-H1G1 and a transformant of mouse myeloma cells J558L or NS-1 transformed with the plasmid pSV2-H1G1 are also provided.

21 Claims, 3 Drawing Sheets

5'-TTGGCGAGCTGGAAGCAGATGATGAATTAG

AGTCAAGATGGCTGCATGGGGGTCTCCGGC

ACCCACAGCAGGTGGCAGGAAGCAGGTCAC

CGCGAGAGTCTATTTTAGGAAGCAAAAAAA

CACAATTGGTAAATTTATCACTTCTGGTTG

TGAAGAGGTGGTTTTGCCAGGCCCAGATCT

GAAAGTGCTCTACTGAGCAAAACAACACTT

GGACAATTTGCGTTTCTAAAATAAGGCGAG

GCTGACCGAAATCGAAAGGCTTTTTTTAAC

TATCTGCAATTTCATTTCCAATCTTAGCTT

ATCAACTGCTAGTTGG-3'

FIG. 4 pSV2-HIGI-a

FIG. 5

5'-TTGGCGAGCTGGAAGCAGATGATGAATTAG

AGTCAAGATGGCTGCATGGGGGTCTCCGGC

ACCCACAGCAGGTGGCAGGAAGCAGGTCAC

CGCGAGAGTCTATTTAGGAAGCAAAAAAA

CACAATTGGTAAATTTATCACTTCTGGTTG

TGAAGAGGTGGTTTTGCCAGGCCCAGATCT

GAAAGTGCTCTACTGAGCAAAACAACACTT

GGACAATTTGCGTTTCTAAAATAAGGCGAG

GCTGACCGAAATCGAAAGGCTTTTTTTAAC

TATCTGCAATTTCATTTCCAATCTTAGCTT

ATCAACTGCTAGTTGG-3'

HUMAN IMMUNOGLOBULIN AND ENHANCER GENE FRAGMENTS

This application is a continuation of application Ser. No. 668,999, filed Nov. 5, 1984, now abandoned.

This invention relates to gene fragments derived from human immunoglobulin genes. More specifically, this invention relates to an enhancer DNA segment derived from a human immunoglobulin gene, a structural gene fragment, a promoter segment and to a human gene fragment based on a combination of these.

In recent years, studies have been made on immunoglobulin genes, and the elucidation of the heavy (H) chain in a human immunoglobulin has been under way. It is well known that the H chain is composed mainly of a site of bonding to an antigen which is a variable region (called V) and a constant region (called C) which has physiological activities such as bonding to a complement or interaction with a specific cell [see "Gendai Kagaku" (Modern Chemistry), November 1981, pages 62-68, published by Baifukan, Tokyo].

Elucidation of the DNA sequence and function of immunoglobulin genes has been done to a considerable extent with regard to mouse genes. It has been found that in the variable region (V) of a mouse immunoglobulin, a V gene, a D gene and a J gene exist in this sequence and a DNA segment having the function of a promoter exists upstream (on the 5' side) of the V gene. Furthermore, it has been presumed that between the J gene and the constant region (C), a DNA segment having the function of markedly enhancing the transcription efficiency, i.e. an enhancer, exists. (See "Gendai Kagaku", November 1983, pages 62-68, published by Baifukan, Tokyo.) It is said that this enhancer exists downstream of the J gene; when it is of the undifferentiated type, it cannot enhance the transcription efficiency because the promoter is remote; but it becomes phenotypic upon recombination in V-J and V-D-J joining and gains the function of enhancing the efficiency of transcription from the promoter existing upstream of the V gene.

Recently, Walter Schaffner et al. reported the DNA sequence of an enhancer in mouse H-chain genes (Cell, Vol. 33, 729-740, July 1983).

Susumu Tonegawa et al. likewise discovered the existence of an enhancer in mouse H-chain genes and its base sequence (see Cell, Vol. 33, 717-728, July 1983).

David Baltimore et al. also reported the existence of an enhancer in the mouse L-chain and its DNA sequence (see Cell, Vol. 33, 741-748, July 1983).

Thus, with regard to the mouse H-chain and L-chain genes, the existence of not only various gene units contained in the variable region (V) and the constant region (C) but also units having various functions such as promoters and enhancers has been elucidated, and the DNA sequences of some of them have been determined.

Before Dec. 6, 1983 which is the filing date of Japanese Patent Application No. 229037/1983 from which the Convention priority of the present application is claimed, the constituent genes and their functions in the H chains of human immunoglobulin genes were gradually elucidated, but the existence of enhancers was only conjectured. The whole DNA sequence of such an enhancer and DNA sequence units that permit performance of its function were not known.

Very recently, T. H. Rabbitts et al. and Susumu Tonegawa et al., independently from each other, reported the DNA sequences of enhancers in the H-chains of human immunoglobulin genes (see Nature, Vol. 306, 806-809, 22/29, December 1983 and ibid., Vol. 307, 334-340, 26 January 1984).

On the other hand, the DNA sequences of the D gene and a promoter contained in the variable region of the H-chain of human immunoglobulin genes have not been known at all.

It is an object of this invention therefore to provide an enhancer DNA segment derived from a human immunoglobulin gene.

Another object of this invention is to provide a gene fragment which contains enhancer DNA segments derived from a structural gene and a human immunoglobulin gene optionally together with a promoter segment derived from a human immunoglobulin gene, and contributes to enhancement of the efficiency of transcription and translation.

Still another object of this invention is to provide a D segment derived from a human immunoglobulin gene.

Yet another object of this invention is to provide a promoter segment derived from a human immunoglobulin gene.

Further objects and advantages of this invention will become apparent from the following description.

The enhancer DNA segment provided by this invention comprises a strand containing at least the following DNA units $E_1$, $E_2$ and $E_3$, unit $E_1$: —AAAACAC— unit $E_2$: —TGGTTGTGAA— unit $E_3$: —GTGGTTTTG— wherein A represents deoxyadenosine 5'-phosphate, C represents deoxycytidine 5'-phosphate, G represents deoxyguanosine 5'-phosphate and T represents deoxythymidine 5'-phosphate, in this sequence and a complementary strand thereof.

The units which can constitute the enhancer DNA segment derived from a human immunoglobulin gene in accordance with this invention are included in the aforesaid sequence. In the direction of sequence, the left side shows a base at the 5'-terminal and the right side, a base at the 3'-terminal. The units $E_1$, $E_2$ and $E_3$ form base pairs with complementary bases. Accordingly, the enhancer DNA segment of this invention comprises a strand containing the units $E_1$, $E_2$ and $E_3$ and a strand (comlementary strand) containing complementary base units forming base pairs with the units $E_1$ to $E_3$.

The enhancer DNA segment of this invention at least contains the units $E_1$, $E_2$ and $E_3$, and preferably not more than 50 base pairs in total.

Preferably, the enhancer DNA segment of this invention comprises a strand containing at least one of the following DNA units $E_5$ and $E_6$.

unit $E_5$: —GTGGCAGG— unit $E_6$: —GGCCCAGAT— wherein A, C, G and T are as defined above, or at least one of the following DNA units $E_4$ and $E_7$ unit $E_4$: —TGATGAAT— unit $E_7$: —TGCAATTT— wherein A, C, G and T are as defined above, in addition to the units $E_1$, $E_2$ and $E_3$.

In the above preferred embodiment, the units $E_5$ and $E_4$ exist before the unit $E_1$ (on the 5' side) and the units $E_6$ and $E_7$ exist after the unit $E_3$ (on the 3' side), and the total number of base pairs can be 150 or less.

An enhancer DNA segment containing the above units $E_1$, $E_2$, $E_3$, $E_5$ and $E_6$ is more preferred, and an enhancer DNA segment containing these units and further at least one of the units $E_4$ and $E_7$ before the unit $E_5$ (in the case of the unit $E_4$) and after the unit $E_6$ (in the case of the unit $E_7$) is particularly advantageous. In this case, the total number of base pairs can be 300 or less.

An example of the enhancer DNA segment of this invention which contains all of the units $E_4$, $E_5$, $E_1$, $E_2$, $E_3$, $E_6$ and $E_7$ in this sequence is one comprising a strand represented by the following DNA sequence $E_o$.

TTGAGCGAAGCTGGAAGCAGATGATGAAT

TAGAGTCAAGATGGCTGCATGGGGGTCTC

CGGCACCCACAGCAGGTGGCAGGAAGCAG

GTCACCGCGAGAGTCTATTTTAGGAAGCA

AAAAAACACAATTGGTAAATTTATCACTT

CTGGTTGTGAAGAGGTGGTTTTGCCCAGG

CCCAGATCTGAAAGTGCTCTACTGAGCAA

AACAACACCTGGACAATTTGCGTTTCTAA

AATAAGGCGAGGCTGACCGAAACTGAAAA

GGCTTTTTTTAACTATCTGCAATTTCATT

TCCAATCTTAGCTTA and a complementary strand thereof.

In the exemplified DNA segment, the following unit $E_t$

TCAACTGCTAGTTGG may be directly bonded to the 3' side of the strand of the above segment $E_o$, or the following unit $E_i$

TTATTTTTTTAATTAA may be directly bonded to the 5' side of the strand of the segment $E_o$.

The enhancer DNA segment of this invention contributes to the expression of protein-forming function derived from a structural gene and to the enhancement of the efficiency of expression of the aforesaid function.

Accordingly, the present invention also provides a gene fragment comprising (a) the enhancer DNA segment of the invention and (b) a structural gene.

Examples of the structural gene constituting the above gene fragment are human structural genes, structural genes of mammals other than humans, particularly human immunoglobulin genes and immunoglobulin genes of mammals other than humans, an insulin gene, and an interferon gene.

The structural genes may, for example, be human immunoglobulin genes such as a human V gene, a human D gene, a human J gene and a human $C_{\gamma 1}$ gene, and human betaglobin gene.

The functions and DNA sequences of these human immunoglobulin protein genes, except the DNA sequences of the D and V genes, are known as follows:

V gene

A gene which codes a variable region of about 100 residual groups from the $NH_2$ end of immunoglobulin molecules.

J gene

A gene which codes a joining portion between the variable region and the constant region of immunoglobulin molecules [see, for example, J. G. Seidman, E. E. Max and P. Leder, Nature, 280, 370 (1979)]

D gene

A gene which exists between the J gene and the V gene and codes that portion of immunoglobulin molecules in which greatest diversity is observed [see, for example, J. Schilling, B. Clevinger, J. M. Davie and L. Hood, Nature, 283, 35 (1980].

$C_{\gamma 1}$ gene

One of genes which code a constant region portion of about 330 residual groups from the COOH terminal of immunoglobulin H-chain molecules. $C_{\gamma 1}$ shows the H-chain of IgG subclass 1.

With regard to the other structural genes, the following function and DNA sequence of the beta-globin gene are known.

beta-Globin gene

A gene that codes globin which is a protein portion of hemoglobin.

The DNA sequences of the D gene and V gene have been elucidated for the first time by the inventors of the present invention and constitute part of the present invention.

The human D gene comprises a strand represented by the following DNA sequence $D_o$

GGCCTCCTCCGGGGGGGCTGGAA

CGACGTGG wherein A, C, G and T are as defined hereinabove, and a complementary strand thereof.

The human V gene is composed of a strand represented by the following DNA sequence $V_o$

CAGGTGCAGCTACACCAGTGGGG

CGCAGGACTGGTGAAGCCTTCGG

AGACCCTGTCCCTCACCTGCGCT

GTCTTTGGTGGGTCCTTCAGTGG

TTACTACTGGAGCTGGATCCGCC

AGCCCCCAGGAAGGGGACTGGAG

TGGATTGGAGAAATCAATCATAG

TGGAAGCACCAATTACAAAACGT

CCCTCAAGAGTCGAGTCACCATA

TCTTTAGACACGTCCAAGAACCT

GTTCTCCCTGAAGCTGAGCTCTG

TGACCGCCGCGGACACGGCTGTG

-continued

TATTACTGTGCGAGG wherein A, C, G and T are as defined hereinabove, and a complementary strand thereof.

The human J gene comprises a strand represented by the following DNA sequence $J_o$

ACTACTACTATGGTATGGACGTC

TGGGGCCAAGGGACCACGGTCAC

CGTCTCCTCA wherein A, C, G and T are as defined, and a complementary strand thereof.

The gene fragment of this invention comprising the enhancer DNA segment (a) and the structural gene (b) contains at least one of the above genes as the structural gene. When the structural genes are the human V gene, human D gene and human J gene, they are preferably joined in this sequence.

Furthermore, in the gene fragment of this invention, the enhancer DNA segment (a) is positioned up to about 5 kilobase pairs (Kbp) from the structural gene (b). Likewise, the structural gene (b) is positioned on the side of the 5' terminal base of the enhancer DNA segment (a).

In the gene fragment of this invention, the human D gene, the human V gene and the human J gene respectively transcribe m-RNA (ribonucleic acid).

The human D gene transcribes a human D m-RNA comprising a strand represented by the following RNA base sequence $RD_o$ ggccuccuccggggggcuggaa cgacgugg wherein a represents adenosine 5'-phosphate, c represents cytidine 5'-phosphate, g represents guanosine 5'-phosphate and u represents uridine 5'-phosphate.

The human V gene transcribes a human V m-RNA comprising a strand repesented by the following RNA base sequence $RV_o$ caggugcagcuacagcaguggg cgcaggacuggugaagccuucgg agacccuguccucaccugcgcu gucuuuggugggguccuucagugg uuacuacuggagcuggauccgcc agccccaggaaggggacuggag uggauuggagaaaucaaucauag uggaagcaccaauuacaaaacgu cccucaagagucgagucaccaua ucuuuagacacguccaagaaccu guucucccugaagcugagcucug ugaccgccgcggacacggcugug uauuacugugcgagg wherein a, c, g and u are as defined hereinabove.

The human J gene transcribes a human J m-RNA comprising a strand represented by the following RNA base sequence $RJ_o$ acuacuacuauggu auggacguc uggggccaagggaccaacgguca ccgucuccuca wherein a, c, g and u are defined as above.

When in the gene fragment of this invention, the structural gene is the human D gene, human V gene or human J gene, each of these genes may be defined by a polypeptide chain which it codes instead of defining it by the aforesaid DNA sequence.

Specifically, the human D gene can be defined as a gene which codes a polypeptide chain represented by the following amino acid sequence $AD_o$ GlyLeuLeuArgGlyGlyTrpAsnAspVal wherein Gly, Leu, Arg, Trp, Asn, Asp and Val respectively represent glycine, leucine, arginine, tryptophan, asparagine, aspartic acid and valine.

The human V gene may be defined as a gene which codes a polypeptide chain represented by the following amino acid sequence $AV_o$ GlnValGlnLeuGlnGlnTrpGlyAlaGly LeuValLysProSerGluThrLeuSerLeu ThrCysAlaValPheGlyGlySerPheSer GlyTyrTyrTrpSerTrpIleArgGlnPro ProGlyArgGlyLeuGluTrpIleGlyGlu IleAsnHisSerGlySerThrAsnTyrLys ThrSerLeuLysSerArgValThrIleSer LeuAspThrSerLysAsnLeuPheSerLeu LysLeuSerSerValThrAlaAlaAspThr AlaValTyrTyrCysAlaArg wherein Gly, Leu, Arg, Trp, Asn, Asp and Val are as defined above, and Ala, Lys, His, Ile, Phe, Ser, Tyr, Thr, Cys, Pro, Met, Glu and Gln repsectively represent alanine, lysine, histidine, isoleucine, phenylalanine, serine, tyrosine, threonine, cystine, proline, methionine, glutamic acid and glutamine.

The human J gene may be defined as a gene which codes a polypeptide chain represented by the following amino acid sequence $AJ_o$ AspTyrTyrTyrGlyMetAspValTrpGly GlnGlyThrThrValThrValSerSer wherein Asp, Tyr, Gly, Met, Asp, Val, Trp, Gly, Gln, Thr, Val and Ser are as defined above.

By the fact that the present inventors elucidated the aforesaid DNA sequences $D_o$ and $V_o$ for the first time, the following four gene fragments also become the subject matters of the present invention as useful human immunoglobulin gene fragments.

(1) A human D gene fragment comprising a strand represented by the above DNA sequence $D_o$ and a complementary strand thereof.

(2) A human V gene fragment comprising a strand represented by the above DNA sequence $V_o$ and a complementary strand thereof.

(3) A human V and D gene fragment comprising a human V gene composed of a strand represented by the above DNA sequence $V_o$ and a complementary strand thereof and a human D gene composed of a strand represented by the above DNA sequence $D_o$ and a complementary strand thereof, the human V gene being positioned on the side of the 5'-terminal base of the human D gene.

(4) A human V, D and J gene fragment comprising a human V gene composed of a strand represented by the above DNA sequence $V_o$ and a complementary strand thereof, a human D gene composed of a strand represented by the above DNA sequence $D_o$ and a complementary strand thereof and a human J gene composed of a strand represented by the above DNA sequence $J_o$ and a complementary strand thereof, the human D gene being positioned between the 3'-terminal base of the human V gene and the 5'-terminal base of the human J gene.

For the same reason, the following four RNA fragments are the subject matters of the present invention as useful human immunoglobulin m-RNA fragments.

(1) A human D m-RNA fragment comprising a strand represented by the above RNA sequence $RD_o$.

(2) A human V m-RNA fragment comprising a strand represented by the above RNA sequence $RV_o$.

(3) Human V and D m-RNA fragments comprising a human D m-RNA comprising a strand represented by the above RNA sequence $RD_o$, and a human V m-RNA comprising a strand represented by the above RNA sequence $RV_o$, the human V m-RNA being positioned on the side of the 5'-terminal base of the human D m-RNA.

(4) A human V, D and J m-RNA fragments comprising a human D m-RNA comprising a strand represented by the above RNA sequence $RD_o$, a human V m-RNA comprising a strand represented by the above RNA base sequence $RV_o$ and a human J m-RNA comprising a strand represented by the above RNA sequence $RJ_o$, the human D m-RNA being positioned between the 3'-terminal base of the human V m-RNA and the 5'-terminal base of the human J m-RNA.

Investigations of the present inventors have now shown the existence of a DNA segment having the function of a promoter in the H-chain of human immunoglobulin genes, which has previously been only conjectured.

Heretofore, mouse immunoglobulin genes have been considerably studied, and it is said that when an undifferentiated immunoglobulin gene is reconstructed into a phenotypic immunoglobulin gene by recombination in V-J and V-D-J joinings, the promoter existing upstream of the V gene has the function of enhancing the efficiency of transcription.

The present inventors have discovered that a promoter segment exists in an intron between the leading region and the variable region in the H-chains of human immunoglobulin genes, and have determined the DNA sequence of the promoter.

It is believed that the promoter segment of this invention, either by itself or in combination with the enhancer DNA segment, has the action of markedly enhancing the efficiency of transcription of not only the V gene, D gene and J gene but also structural genes to be replicated, transcribed or translated. Accordingly, the promoter segment of this invention is expected to be very useful for the production of large quantities of proteins, for example human monoclonal antibodies.

Accordingly, the present invention provides a gene fragment comprising (a) the enhancer DNA segment of the invention described above, (b) a structural gene, and (c) a promoter segment comprising a strand having at least one unit selected from the group consisting of the following DNA sequence unit $P_1$

GGGTTTGGTGAGGGGAGGCCACAGGAAGAG

AACTGAGTTCTCAGAGGGCACAGCCAGCAT

ACACCTCCCAGGTGAGCCCAAAAGACTGGG

GCCTCCCCTATCCCTTTTTACCTACCCATA

CAAAGGCACCACCCACATGCAAATCCTCAC

TTAGGCACCCACAGGAAATGACTACACATT

TCCTTAAAATCAGGGTCCAGCT wherein A, C, G and T are as defined hereinabove, the following DNA sequence unit $P_2$

AGTGTCTCACCAATGCGGATATGAAGATAT

GAGATGCTGCCTCTGATCCCAGGGCTCACT

GTGGGTTTCTCTGTTCACAGGGGT wherein A, C, G and T are as defined hereinabove, and the following DNA sequence unit $P_3$

AGTGTCTCACCAATGCGGATATGAAGATAT

GAGATGCTGCCTCTGATCCCAAGGCTCACT

GTGGGTTTCTCTGTTCACAGGGGT wherein A, C, G and T are as defined hereinabove, the structural gene (b) being positioned between the enhancer DNA segment (a) and the promoter segment (c).

In the above gene fragment, the enhancer DNA segment (a) is positioned preferably up to about 5 Kbp away from the structural gene (b), and the promoter segment (c) is positioned preferably up to about 5 Kbp away from the structural gene (b).

In the above gene fragment, the above promoter segment may contain one or more of the above DNA sequence units $P_1$, $P_2$ and $P_3$. Preferably, the promoter segment contains the DNA sequence units $P_1$, $P_2$ and $P_3$, and more preferably in such a relation that $P_1$ is positioned on the side of the 5'-terminal base of $P_2$, and $P_2$ is positioned on the side of the 5'-terminal base of $P_3$.

With regard to the sequence of (a), (b) and (c), it is preferred that the promoter segment (c) is positioned on the side of the 5'-terminal base of the structural gene (b), and the structural gene (b) is positioned on the side of the 5'-terminal base of the enhancer DNA segment (a).

By the fact that the above promoter sequence has been elucidated for the first time by the present inventors, the present invention also provides a promoter segment comprising a strand containing at least one unit selected from the group consisting of the above DNA sequence unit $P_1$, the above DNA sequence unit $P_2$ and the above DNA sequence unit $P_3$, wherein preferably the DNA sequence unit $P_1$ is positioned on the side of the 5'-terminal base of the DNA sequence unit $P_2$ and the unit $P_2$ is positioned on the side of the 5'-terminal base of the DNA sequence unit $P_3$.

The relative positions of the enhancer DNA segment, the immunoglobulin gene and the promoter segment in a human chromosomal DNA will be described below with reference to the accompanying drawings.

Figure 1:
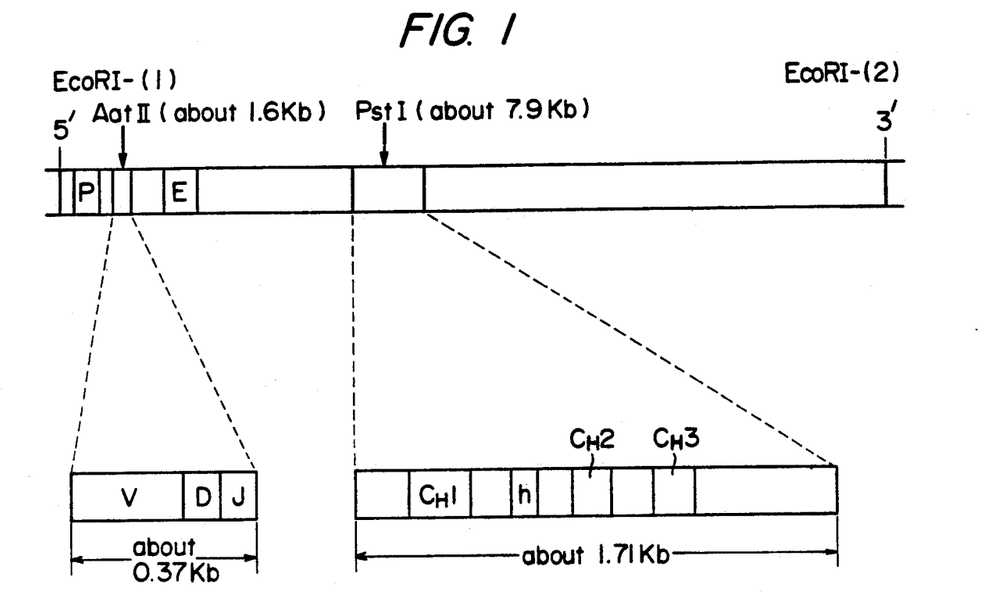
FIG. 1 is a view schematically showing unit existing between sites of cleavage by restriction endonuclease EcoRI in a human chromosomal DNA containing an immunoglobulin gene.

More specifically:

FIG. 1 is a view schematically showing units existing between sites of cleavage by restriction endonuclease Eco RI in a human chromosomal DNA containng an immunoglobulin gene.

In FIG. 1, 5' and 3' specify terminal bases at the cleavage sites of a fragment containing an immunoglobulin gene obtained by cleaving the human chromosomal DNA with restriction endonuclease Eco RI. The distance betweeen the 5'-terminal base and the 3'-terminal base is about 21 Kb (21±1- Kb).

The part shown by an arrow as Aat II in the fragment is a site at which the fragment can be cleaved by restriction endonuclease Aat II and is about 1.6 Kb (1.6 Kb±0.1 Kb) away from the 5'-terminal.

The human V gene, human D gene and human J gene provided by the present invention are positioned in this sequence as viewed from the 5'-terminal between a site about 0.33 Kb (0.33 Kb±0.02 Kb) toward the 5'-terminal from the Aat II cleavable site and a site about 0.04 Kb (0.04 Kb±0.005 Kb) toward the 3'-terminal from the Aat II cleavable site, the two sites being apart from each other by a length of about 0.37 Kb (0.37 Kb±0.025 Kb)

The part shown by an arrow as Pst I in FIG. 1 shows that site of the fragment which can be cleaved by restriction endonuclease Pst I and is about 7.9 Kb (7.9 Kb ±0.5 Kb) away from the 5'-terminal.

The human $C_{\gamma 1}$ gene used as one human immunoglobulin gene in this invention exists between a site about 0.69 Kb (0.69 Kb±0.02 Kb) toward the 5'-terminal from the site of cleavage with Pst I and a site about 1.02 Kb (1.03 Kb±0.03 Kb) toward the 3'-terminal from it, the two sites being apart from each other by a length of about 1.71 Kb (1.71 Kb±0.05 Kb). The human gene $C_{\gamma 1}$ contains regions called a $C_H1$ region, an h region, a C region and a $C_H3$ region in this sequence as viewed from the 5'-terminal. A stop codon exists at a position about 1.02 Kb toward the 3'-terminal from the Pst I cleavage site.

P in FIG. 1 shows the position of the promoter segment provided by this invention having the function of a promoter which is located on the side of the 5'-terminal with respect to the portion having a length of about 0.37 Kb determined with the Aat II cleavage site as a standard.

E in FIG. 1 shows the position of the enhancer DNA segment provided by this invention having the function of an enhancer which is located on the 3' side with respect to the portion having a length of about 0.37 Kb determined with the Aat II cleavage site as a standard and on the 5' side with respect to the portion having a length of about 1.71 Kb determined with the Pst I cleavage site as a standard.

As a gene fragment containing the largest amount of a DNA segment derived from a human gene, the present invention provides a human immunoglobulin gene fragment being present in a fragment obtained by cleavage of a human chromosomal DNA segment containing a human immunoglobulin gene with restriction endonuclease Eco RI and comprising (1) a DNA unit containing a human V gene, a human D gene and a human J gene in this sequence and existing within a region interposed between a site about 0.33 Kb toward the 5'-terminal base with respect to that site of said fragment which can be cleaved with restriction endonuclease Aat II and exists about 1.6 Kbp away from the 5'-terminal base of the fragment, and a site about 0.04 Kbp toward the 3'-terminal base with respect to said Aat II cleavage site, (2) a DNA base unit containing a human $C_{\gamma 1}$ gene and existing within a region interposed between a site about 0.69 Kbp toward the 5'-terminal base with resepct to that site of the fragment which can be cleaved with restriction endonuclease Pst I and is about 7.6 Kbp away from the 5'-terminal base and a site about 1.02 Kbp toward the 3'-terminal base with respect to said Pst I cleavage site, (3) a promoter unit positioned away from the DNA unit (1) toward the 5'-terminal base, and (4) an enhancer DNA unit positioned between the DNA unit (1) and the DNA unit (2).

The gene fragments in accordance with this invention have the function of expressing of human immunoglobulin H-chain.

A specific procedure of forming a human immunoglobulin H-chain by the gene fragments in accordance with this invention will be described.

The human immunoglobulin gene fragment containing the units (1) to (4) described above is inserted into a vector to form a hybrid DNA.

Examples of such a vector are phage vectors for *Escherichia coli*, such as Charon 4A, Charon 28 and λgtWES.γB; plasmid vectors for *Escherichia coli*, such as pBR322, pBR325 and pMB9; plasmid vectors for *Bacillus subtilis*, such as pUB110 and pHW1; plasmid vectors for yeast, such as YEp13, pJDB219, YRp7, YRp16, YIp5 and YIp32; plasmid vectors for animal cells, such as pSV2-gpt and pKSV-10; and plasmid vectors for plant cells such as pTiB6-806. These vectors are merely illustrative, and needless to say, other vectors may also be used.

For example, Charon 4A phage vector is cleaved with restriction endonuclease Eco RI to give two phage DNA fragments corresponding to the right arm and the left arm. The aforesaid human DNA fragment having a length of about 21 Kb obtained by cleaving a human chromosomal DNA segment containing a human immunoglobulin with restriction endonuclease Eco RI is ligated between the two phage DNA fragments by a ligase such as T4-DNA ligase to prepare a hybrid DNA. To obtain the hybrid DNA in large quantities, the resulting hybrid DNA is packed, for example, in Charon 4A phage to prepare a human gene library containing the human gene fragment. The human gene library, i.e. an assembly of phages containing the human gene fragment, is then infected with, for example, *Escherichia coli* and cultivated to obtain a clone containing the human gene. The aforesaid hybrid DNA containing the human gene can be prepared in large quantities from this clone.

The hybrid DNA is digested with a suitable restriction endonuclease to obtain a large amount of the desired human gene fragment. To obtain the human gene fragment in large amounts, it is inserted, for example, into an *E. coli* plasmid to prepare a hybrid DNA which is then propagated in *E. coli*. Examples of the hybrid DNA inserted in the *E. coli* plasmid are shown below.

(1) A hybrid DNA (pTJ3 in FIG. 3) comprising a pBR322 fragment having a length of about 4.4 Kb obtained by digesting *E. coli* plasmid pBR322 with restriction endonucleases Hind III and Eco RI, and ligated with the PBR322 fragment, a human DNA fragment having a length of about 3.4 Kb which exists within a DNA fragment having a length of about 21 Kb obtained by cleaving a human chromosomal DNA segment containing a human immunoglobulin with restriction endonuclease Eco RI and is interposed between the 5'-terminal position [Eco RI-(1)] to be cleaved with restriction endonuclease Eco RI and the 3'-terminal position [Hind III-(1)] to be cleaved with restriction endonuclease Hind III.

(2) A hybrid DNA (pTJ7 in FIG. 3) comprising a pBR322 fragment having a length of about 4.4 Kb obtained by digesting *E. coli* plasmid pBR322 with restriction endonuclease Bam HI, and ligated with the pBR322 fragment, a human DNA fragment having a length of about 0.8 Kb which exists within a fragment having a size of about 3.4 Kb interposed between the Eco RI-(1) position and the Hind III-(1) position, and which is interposed between the 5'-terminal position [Bam HI-(1)] and the 3'-terminal position [Bam HI-(2)] to be cleaved with restriction endonuclease Bam HI.

(3) A hybrid DNA (pTJ2 in FIG. 3) comprising a pBR322 fragment having a length of about 4.4 Kb obtained by digesting *E. coli* plasmid pBR322 with restriction endonuclease Hind III and ligated with the pBR322 fragment, a human DNA fragment having a length of about 3.6 Kb which exists within a DNA fragment having a length of about 21 Kb obtained by cleaving a human chromosomal DNA segment containing a human immunoglobulin with restriction endonuclease Eco RI and is interposed between the 5'-terminal position [Hind III-(2)] and the 3'-terminal position [Hind III-(2)] to be cleaved with restriction endonuclease Hind III.

(4) A hybrid DNA (pTJ1B and pTJ1BR in FIG. 3) comprising a pBR322 fragment having a length of about 4.4 Kb obtained by digesting *E. coli* plasmid pBR322 with restriction endonuclease Hind III, and ligated with the pBR322 fragment, a human DNA fragment having a length of about 8.2 Kb which exists within a DNA fragment having a length of about 21 Kb obtained by cleaving a human chromosomal DNA segment containing a human immunoglobulin protein with restriction endonuclease Eco RI and is interposed between the 5'-terminal position [Hind III-(2)] and 3'-terminal position [Hind III-(3)] to be cleaved with restriction endonuclease Hind III.

(5) A hybrid DNA (pTJ5 in FIG. 3) comprising a pBR322 fragment having a length of about 4.4 Kb obtained by digesting *E. coli* plasmid pBR322 with restriction endonuclease Pst I, and ligated with the pBR322 fragment, a human DNA fragment having a length of about 1.7 Kb which exists within a fragment having a length of bout 8.2 Kb interposed between the Hind III-(2) position and the Hind III-(3) position, and which is interposed between the 5'-terminal position [Pst I-(2)] and the 3'-terminal position [Pst I-(3)] to be cleaved with restriction endonuclease Pst I.

(6) A hybrid DNA (pTJ4 in FIG. 3) comprising a pBR322 fragment having a length of about 4.4 Kb obtained by digesting *E. coli* plasmid pBR322 with restriction endonuclease Hind III, and ligated with the pBR322 fragment, a human DNA fragment having a length of about 1.7 Kb which exists within a fragment having a length of about 8.2 Kb interposed between the Hind III-(2) position and the Hind III-(3) position with the portion ranging from the Pst I-(2) position to a Pst I site closest to the Hind III-(3) located between the Hind III-(3) position and the Pst I-(3) position being deleted.

To prepare each of the hybrid DNAs (1) to (6) in large quantities, *E. coli* such as *E. coli* C600 strain, for example, is transformed with each of these hybrid DNAs to obtain a transformant.

Likewise, to obtain the aforesaid human DNA fragment having a length of about 21 Kb in large quantities, the following plasmid or transformant, for example, is prepared.

Plasmid pSV2-HIG1 which is a hybrid DNA obtained by inserting a human DNA fragment having a length of about 21 Kb obtained by cleaving a human chromosomal DNA segment containing a human immunoglobulin with restriction endonuclease Eco RI into the Eco RI site of vector pSV-2gpt cleaved with restriction endonuclease Eco RI.

A transformant of *E. coli* MC 1000 strain obtained by transforming the *E. coli* strain with the above plasmid pSV2-HIG1.

The formation of a human immunoglobulin H-chain was actually confirmed by preparing a transformant of mouse myeloma J558L or NS-1 transformed with the above plasmid pSV2-HIG1, and propagating the resulting transformant.

The following Examples illustrate in detail the isolation of a human chromosomal DNA, the preparation of a human gene library, screening of human immunoglobulin genes, the preparation of restriction endonuclease cleavage maps of human immunoglobulin genes, cloning of human immunoglobulin genes, determination of DNA sequences of human immunoglobulin genes, and expression of human immunoglobulin genes in cells.

EXAMPLE 1

Isolation of a human chromosomal DNA:

Human cultivated cells ARH77 ($3 \times 10^8$ cells) were crushed by a glass rod and treated with Protease K (a product of Sigma Co.) in the presence of 2% sodium dodecylsulfate (SDS). Then, phenol saturated with 10 mM Tris HCl (pH 8.0)-1 mM EDTA aqueous solution was added. The mixture was centrifuged to separate it into an aqueous layer and a phenol layer. The aqueous layer was dialyzed against 20 mM Tris HCl (pH 7.5)-100 mM NaCl-5 mM EDTA aqueous solution. The dialyzate was treated with Ribonuclease A (a product of Sigma Co.) and after phenol extraction, dialyzed against 10 mM Tris HCl (pH 8.0)-1 mM EDTA aqueous solution to obtain about 1.2 mg of a human chromosomal DNA [see N. Blin and D. W. Stafford, Nucleic Acids Res., 3, 2303 (1976)].

EXAMPLE 2

Preparation of a human gene library

The human chromosomal DNA (150 micrograms) obtained in Example 1 was partially digested with restriction endonuclease Eco RI (produced by Takara Shuzo Co., Ltd.) in acccordance with the method shown in Example 4, and then subjected to sucrose density gradient centrifugation sucrose 10-40% (wt/vol), 28,000 rpm×15 hours, 20° C.] to obtain 4.3 micrograms of a DNA fragment having a size corresponding to 15 Kb to 23 Kb. The DNA fragment (0.8 microgram) was ligated with Charon 4A vector [see F. R. Blattner, B. G. Williams, A. E. Blechl, K. D. Thompson, H. E. Faber, L. A. Furlong, D. J. Grunward, D. O. Kiefrr, D. O. Moore, J. W. Schumm, F. L. Sheldon and Smithies, Science, 196, 161 (1977)] to obtain a hybrid DNA in which the human DNA was inserted between the right arm and left arm of Charon 4A vector. T4 DNA ligase (a product of Bethesda Research Laboratory). The ligating reaction was carried out at 11° C. for 12 hours in 66 mM Tris-HCl (pH 7.6)-6.6 mM MgCl$_2$-10 mM dithiothreitol-1 mM ATP aqueous solution. The resulting hybrid DNA was packaged in vitro [A. Becker and M. Gold, Proc. Natl. Acad. Sci. U. S., 72, 581 (1975)]to form a human gene library (1.8×10$^6$ PFU/$\mu$g-DNA, containing more than 99% of human DNA).

EXAMPLE 3

Screening of human genes

E. coli LE 392 strain was, infected with the gene library (an assembly of Charon 4A phages containing DNAs derived from human) obtained in Example 2 to form plaques. A clone containing a human immunoglobulin gene was selected in accordance with the plaque hybridization method of Benton and Davis [see W. D. Benton and R. W.

Davis, Science, 196, 180 (1977)] using a $^{32}$P-labelled human immunoglobulin H-chain J gene. DNA was prepared from the Charon 4A phages containing a human immunoglobulin gene by the method of Thomas and Davis [M. Thomas and R. W. Davis, J. Mol. Biol., 91, 315 (1974)].

EXAMPLE 4

Preparation of a restriction endonuclease cleavage map

One microgram of the Charon 4A DNA containing a human immunoglobulin gene obtained in Example 3 was dissolved in 20 microliters of a buffer for digestion with restriction endonucleases [50 mM Tris-HCl (pH 7.4}-100 mM ( NaCl-10 mM MgSO$_4$ aqueous solution for Eco RI, Mlu I or Sph I; 10mM Tris-HCl (pH 7.5)-60 mM NaCl-7 mM MgCl$_2$ aqueous solution for Aat II, Ava I, Bam HI, Bst EII, Hind III, Pst I or Pvu II; 10 mM Tris-HCl (pH 7.4)-10 mM MgSO$_4$-1 mM dithiothreitol aqueous solution for Bgl II; and 10 mM p Tris-HCl (pH 8.0)-20 mM KCl-7 mM MgCl$_2$-7 mM 2-mercaptoethanol solution for Hpa I], and digested with two units of a restriction endonuclease (Aat II was a product of Toyobo Ltd.; Ava I was a product of Bethesda Research Laboratories, Inc.; Bst EII and Sph I were products of New England Biolabs, Inc.; and the other endonucleases were products of Takara Shuzo Co., Ltd.) at 37° C. for more than 1 hour. When the digestion was carried out by using two restriction endonucleases, there was used a procedure comprising first treating the DNA with a restriction endonuclease acting at a low salt concentration, then increasing the salt concentration to a predetermined concentration, and treating DNA with another restriction endonuuclease acting at a higher salt concentration.

After the digestion, 4 microliters of an aqueous solution containing 0.25% of bromophenol blue and 50% of glycerol, was added and the mixture was subjected to 0.8%-2.5% agarose gel electrophoresis. The agarose used was type II made by Sigma Co. designed for electrophoresis. A 40 mM Tris-CH$_3$COOH (pH 8.0)-1 mM EDTA aqueous solution was used as an electrophoresis running buffer. With a vertical gel having a thickness of 2 mm, the electrophoresis was carried out at a voltage of 6 to 9 V/cm for 1.5 to 3 hours. A product of digestion of $\lambda$ phage DNA with Hind III (made by Boeling Manheim) was used as a molecular size marker for DNA fragments. After the electrophoresis, the DNA in the agarose gel was dyed with a 2 $\mu$g/ml aqueous solution of ethidium bromide, and by irradiating long wavelength ultraviolet light onto the gel, the digestion pattern was observed. By analyzing the patterns of digestion with the various restriction endonucleases either alone or in a combination of two, the relative positions of the restriction endonuclease cleavage sites were determined.

EXAMPLE 5

Recloning of a human immunoglobulin gene (a hybrid DNA of 3.4 Kb Eco RI/Hind III fragment and E. coli plasmid pBR322 including a promoter region, a V-D-J region and an enhancer region Three micrograms of a Charon 4A DNA containing a human immunoglobulin gene was digested with restriction endonucleases Hind III and Eco RI, and subjected to agarose gel electrophoresis (gel concentration 0.8%). A band corresponding to DNA having a size of 3.4 Kb containing a promoter region, a V-D-J region and an enhancer region was cut out, and the agarose gel slice was dissolved in thrice its amount (vol./wt.) of a 8M aqueous solution of NaClO$_4$. By the glass filter method of Chen and Thomas [C. W. Chen and C. A. Thomas Jr., Anal. Biochem., 101, 399 (1980)], a DNA fragment having a size of 3.4 Kb was recovered from the agarose gel.

Separately, one microgram of E. coli plasmid pBR322 was digested with restriction endonuclease Hind III and Eco RI, and 0.5 unit of alkaline phosphatase (E. coli C75 produced by Takara Shuzo Co., Ltd.) was added. They were reacted at 45° C. for 1 hour. After the reaction, the reaction mixture was reaction mixture was exracted three times with phenol in order to deactivate and remove the alkaline phosphatase in it.

The resulting alkaline phosphatase-treated product of the above digestion product (pBR322 digested with Hind III/Eco RI) was mixed with an aqueous solution of a DNA fragment having a size of 3.4 Kb digested with Eco RI/Hind III. The mixture was precipitated with ethanol, and the precipitate was dissolved in 50 microliters of a buffer for ligation (see Example 2). Two units of T4 DNA ligase was added and reacted at 11° C. for 12 hours to obtain a hybrid DNA.

*E. coli* C600 strain was transformed with the hybrid DNA by an improved version of the usual CaCl$_2$ method [M. V. Norgard, K. Keen and J. J. Monaham, Gene. 3, 297 (1978)]. Specifically, *E. coli* C600 strain cultivated for 18 hours was inoculated in 5 ml of L-broth (1% tryptone, 0.5% yeast extract, 0.5% NaCl, pH 7.2) and grown to an extent corresponding to an optical density at 600 nm of 0.3. The cells were washed twice in a cold magnesium buffer [0.11M NaCl-5 mM MgCl$_2$-5 mM Tris-HCl (pH 7.6, 0° C.)], re-suspended in 2 ml of a cold calcium buffer [100 mM CaCl$_2$-250 mM KCl-5 mM MgCl$_2$-5 mM Tris-HCl (pH 7.6, 0° C.)], and left to stand at 0° C. for 25 hours. The cells were then concentrated to one-tenth of their volume in a calcium buffer, and mixed with an aqueous solution of the hybrid DNA in a ratio of 2:1 (vol:vol). The mixture was maintained at 0° C. for 60 minutes, and after adding 1 ml of LBG-broth (1% tryptone, 0.5% yeast extract, 1% NaCl, 0.08% glucose, pH 7.2), cultivated at 37° C. for 1 hour. The culture fluid was inoculated in a selective medium (an L-broth plate containing 30 micrograms/ml of ampicillin) at a rate of 100 microliters/plate. The plate was cultivated overnight at 37° C. to grow the transformant. A DNA was prepared from the resulting colony by a known method, and by agarose gel electrophoresis, the existence of the desired hybrid DNA was determined.

EXAMPLE 6

Recloning of a human immunoglobulin gene (a hybrid DNA of a 8.2 Kb Hind III fragment containing a human C$_{\gamma 1}$ gene and *E. coli* plasmid pBR322):

Three micrograms of Charon 4A DNA containing a human immunoglobulin gene was digested with Hind III substantially in accordance with the method of Example 4, and subjected to agarose gel electrophoresis (gel concentration 0.8%). A band corresponding to DNA having a size of 8.2 Kb and containing a C$_{\gamma 1}$ gene was cut out and the agarose gel slice was dissolved in three times (vol/wt) its amount of an 8M aqueous NaClO$_4$ solution. A DNA fragment having a size of 8.2 Kb was recovered from the agarose gel by the glass filter method of Chen and Thomas [C. W. Chen and C. A. Thomas Jr., Anal. Biochem. 101, 339 (1980)].

Separately, 1 microgram of E. coli plasmid pBR322 was digested with Hind III in accordance with Example 4, and reacted with 0.5 unit of alkaline phosphatase (*E. coli* C75) (a product of Takara Shuzo Co., Ltd.) at 45° C. for 1 hour. After the reaction, the reaction mixture was extracted with phenol three times in order to deactivate and remove the alkaline phosphatase in the reaction mixture.

The alkaline phosphatase treated product of the above digested pBR322 was mixed with an aqueous solution of the 8.2Kb Hind III fragment recovered from the agarose gel. The mixture was precipitated with ethanol, and the precipitate was dissolved in 50 microliters of a buffer for ligation (see Example 2). Two units of T4-DNA ligase was added, and the reaction was carried out at 11° C. for 12 hours to give a hybrid DNA.

*E. coli* C600 strain was transformed, and the transformant was grown, in the same way as in Example 5. DNA was prepared from the resulting colony by a known method, and the existence of the desired hybrid DNA was determined by agarose gel electrophoresis.

Restriction endonuclease cleavage map of subclones

Figure 2:
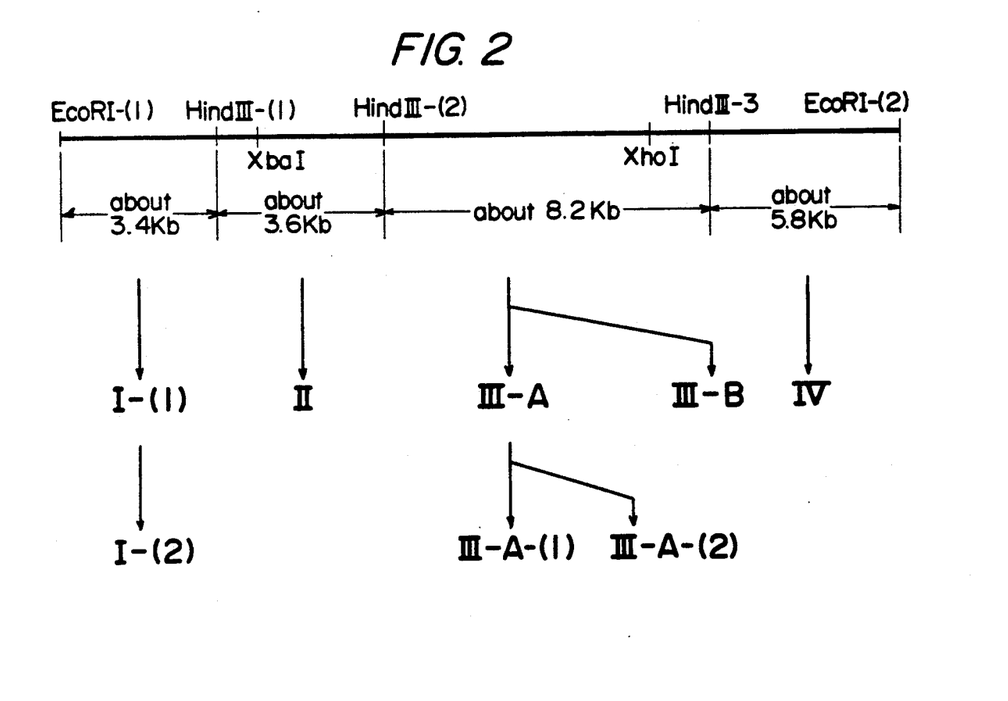
FIG. 2 shows a partial restriction map of a 21 kbp DNA fragment containing a human antibody H-chain gene, and a strategy of subcloning.
Figure 3:
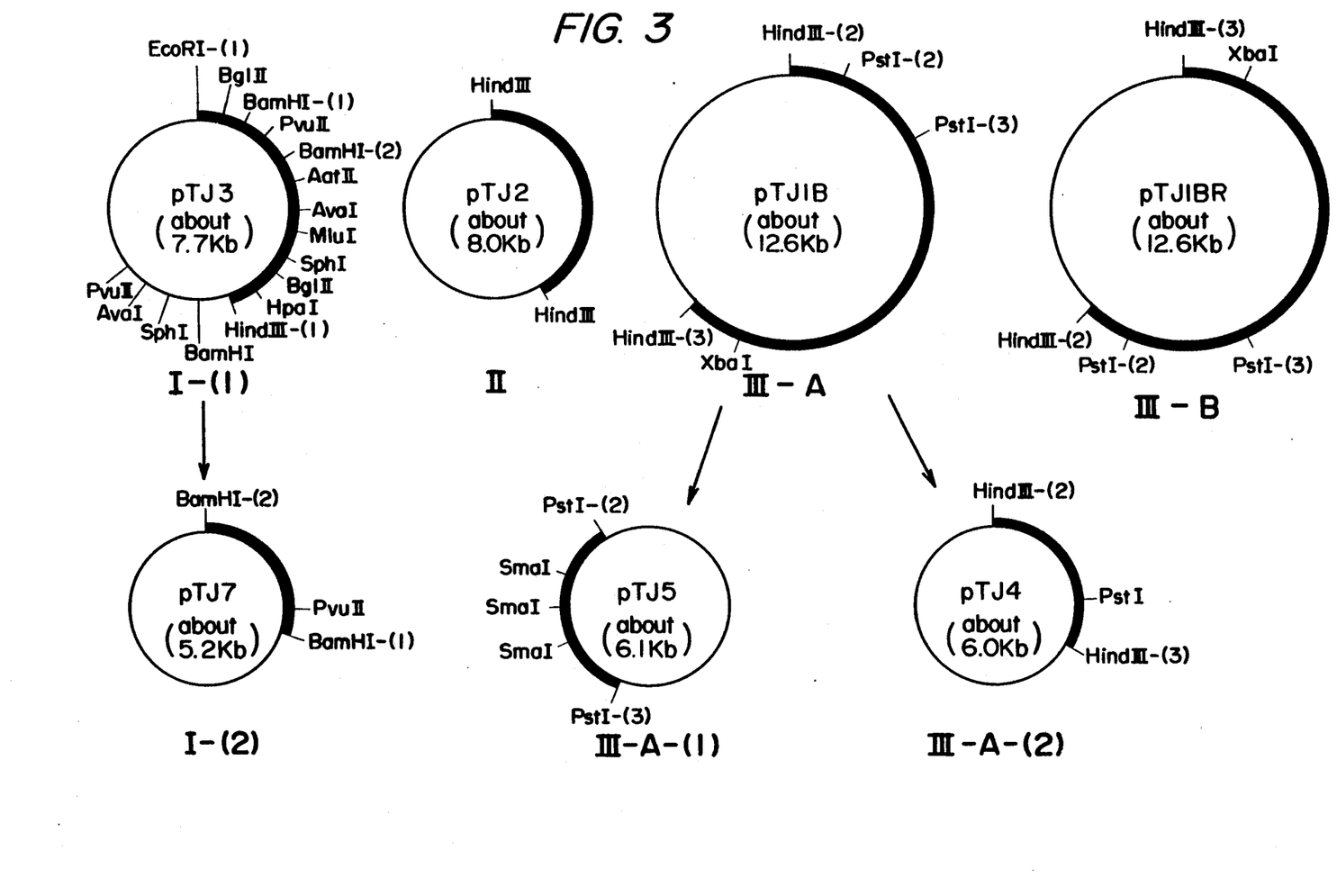
FIG. 3 shows a partial restriction map of various subclones having DNA fragments containing portions of human antibody H-chain gene.

In Examples 4 to 6, subclones having the restriction endonuclease cleavage maps shown in FIGS. 2 and 3 of the accompanying drawings were obtained.

FIG. 2 shows fragments obtained by cleaving a human chromosomal DNA containing an immunoglobulin gene with restriction endonuclease Eco RI. The 5'-terminal position is indicated as Eco RI-(1), and the 3'-terminal position, as Eco RI-(2). FIG. 2 also shows sites at which the DNA fragment can be cleaved with restriction endonuclease Xba I and Xho I. This fragment was cleaved with restriction endonuclease Hind III and divided into four small fragments shown in FIG. 2. Each fragment was inserted into *E. coli* plasmid vector pBR322 to obtain 7 subclones shown in FIG. 3.

Subclone pTJ3

Obtained by inserting a small DNA fragment (about 3.4 Kb) interposed beween Eco RI-(1) and Hind III-(1) into a site between Eco RI and Hind III. A detailed restriction endonuclease cleavage map of this subclone is shown in FIG. 3, I-(1).

Subclone pTJ7

Obtained by inserting a small DNA fragment (about 0.8 Kb) existing between Bam HI-(1) and Bam HI-(2) of the above subclone pTJ3 into the Bam HI site of pBR322. The restriction endonuclease cleavage map of this subclone is shown in FIG. 3, I-(2).

Subclone pTJ2

Obtained by inserting a small DNA fragment (about 3.6 Kb) interposed between Hind III-(1) and Hind III-(2) into the Hind III site of pBR322. The endonuclease cleavage map of this subclone is shown in FIG. 3, II.

Subclone pTJ1B

Obtained by inserting a small DNA fragment (about 8.2 Kb) interposed between Hind III-(2) and Hind III-(3) into the Hind III site of pBR322. The restriction endonuclease cleavage site map of this subclone is shown in FIG. 3, III-A was determined. The presence of 3 to 4 Pst I sites between Pst I-(3) and Hind III-(3) in FIG. III-A.

Subclone pTJ1BR

Obtained by insertion into pBR322 in the same way as in the preparation of pTJ1B above, but the orientation is reverse to that in pTJ1B. The restriction endonuclease cleavage map of this subclone is shown in FIG. 3, III-B.

Subclone pTJ5

Obtained by inserting a small DNA fragment existing between Pst I-(2) and Pst I-(3) of the above subclone pTJ1B into the Pst I site of pBR322. The restriction endonuclease cleavage map of this subclone is shown in FIG. 3, III-A-(1).

Subclone pTJ4

Obtained by deleting from the above subclone pTJ1B a portion ranging from a Pst I site closest to Hind III-(3) existing between Hind III-(3) and Pst I-(3) to Pst I-(2). The restriction endonuclease cleavage map of this subclone is shown in FIG. 3, III-A-(2).

EXAMPLE 7

Determination of the sequence of DNA

The DNA sequences of the enhancer region and the V-D region of the H-chain of a human immunoglobulin gene were determined by the Maxam-Gilbert method [A. Maxam and W. Gilbert, Methods Enzymol., 65, 499 (1980)].

About 50 micrograms of the subclone pTJ3 DNA prepared in Example 6 was digested with Bst EII in accordance with the method of Example 4. The resulting DNA fragment was dephosphorylated with alkaline phosphatase, and labelled with [γ-32P] ATP using 5 units of polynucleotidekinase (produced by P-L Biochemicals Co.). The polynucleotidekinase reaction was carried out in a 50 mM Tris-HCl (pH 9.5)-10 mM MgCl2-5 mM dithiothreitol aqueous solution, and [γ-32P] ATP (made by Amersham Co.) was used in an amount corresponding to 100 micro Ci. The 32P-labelled DNA fragment was digested with Hpa I. The desired DNA fragment was separated by polyacrylamide gel electrophoresis (gel concentration 5%) and extracted from the gel. The resulting 32P-labelled Bst EII/Hpa I fragment was subjected to a partial hydrolysis reaction specific for each of the bases, and subjected to electrophoresis on polyacrylamide gel containing 7M urea (gel concentration 8% to 23%). The separated fragment was subjected to autoradiography at −80° C. for 2 to 7 days, and the cleavage pattern was analyzed to obtain data for the determination of the DNA sequence of the enhancer region.

From a 32P-labelled-Bam HI/Aat II fragment obtained by the above method except using Bam HI instead of Bst EII, data for the determination of the DNA sequence of the V-D region were obtained.

When pTJ3 was digested with Aat II, labelling with [γ-32] ddATP was carried out using a 3'-terminal labelling kit (a product of Amersham Co.). This 32P-labelled DNA fragment was digested with Bam HI, and the desired DNA fragment was separated and recovered by polyacrylamide gel electrophoresis (gel concentration 5%). The resulting 32P-labelled Aat II/Bam HI fragment was also analyzed in accordance with the above procedure to obtain data for the determination of the DNA sequence of the D region.

Figure 5:
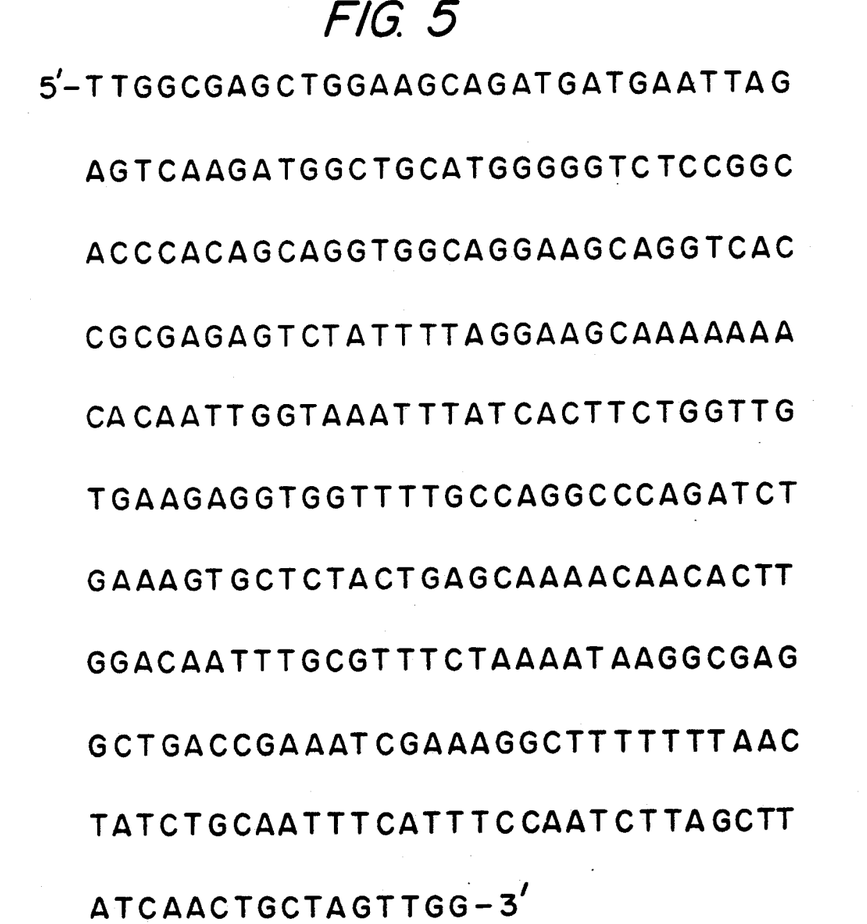
FIG. 5 is an illustration of the nucleotide sequences of DNA comprising an enhancer element located on a major intron of $\gamma_1$ heavy chain human gene.

Thus, the DNA sequences including the enhancer DNA sequence of this invention shown in FIG. 5 were determined.

EXAMPLE 8

Determination of the DNA base sequence

The DNA sequence of the promoter region of a human immunoglobulin gene was determined by the Maxam-Gilbert method [A. Maxam and W. Gilbert, Methods Enzymol., 65, 499 (1980)].

About 50 micrograms of the subclone pTJ3 DNA prepared in Example 5 was digested with Bam HI in accordance with Example 4. The resulting DNA fragment was dephosphorylated with alkaline phosphatase, and labelled with [γ-32P] ATP using 5 units of polynucleotidekinase (a product of P-L Biochemicals Co.). The kination was carried out in a 50 mM Tris-HCl(pH 9.5)-10 mM MgCl2-5 mM dithiothreitol aqueous solution, and [γ-32P] ATP made by Amersham Co. was used in an amount corresponding to 100 micro Ci. The 32P-labelled DNA fragment was digested with Ban I. The desired DNA fragment was separated by electrophoresis on polyacrylamide gel containing 7 M urea (gel concentration 8% to 23%). The DNA fragment was subjected to autoradiography at −80° C. for 2 to 7 days, and the cleavage pattern was analyzed to obtain data for the determination of the base sequence of the promoter region.

EXAMPLE 9

Determination of the DNA base sequence

The base sequence of the constant region of a human immunoglobulin gene was determined by the Maxam-Gilbert method [A. Maxam and W. Gilbert, Methods Enzymol., 65, 499 (1980)].

pTJ5 was digested with Pst I, and labelled with [γ-32P] ddATP using a 3'-terminal labelling kit (made by Amersham Co.). The 32P-labelled DNA fragment was digested with Sma I, and the desired DNA fragment was separated and recovered by polyacrylamide gel elecrophoresis (gel concentration 5%). The resulting 32P-labelled Pst I/Sma I DNA fragment was subjected to a partial hydrolysis reaction specific for each of the bases, and separated by electrophoresis on polyacrylamide gel containing 7M urea (gel concentration 8% to 23%). Then, the DNA fragment was subjected to autoradiography at −80° C. for 2 to 7 days. The cleavage pattern was then analyzed to obtain data for the determination of the DNA sequence of the constant region.

EXAMPLE 10

Expression of a DNA fragment in a cell (1) About $1 \times 10^{10}$ ARH77 cells were homogenized and treated with phenol-cresol to obtain about 6 mg of total RNA. Four milligrams of this RNA was purified through a column of Oligo dT to give 140 mirograms of poly-(A)RNA. Northern hybridization was carried out using 10 micrograms of total RNA and 500 ng of poly-(A)RNA and $2 \times 10^7$ cpm of 2.0 Kb Bam HI/Hind III fragment containing human IgG V-D-J gene as a probe. A band assigned to H-chain m-RNA was detected at 18S, and a band assigned to H-chain m-RNA of membrane type was detected at 23S.

By using the same probe, southern hybridization of a fragment obtained by complete digestion of total RNA of ARH77 with Eco RI was carried out. Two bands were obtained at about 21 Kbp and 9 Kbp respectively, and two allelic genes were detected.

Figure 4:
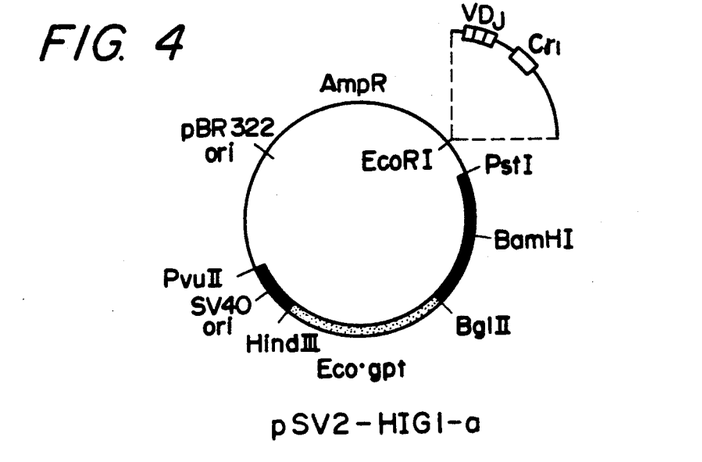
FIG. 4 shows a partial restriction map of plasmid pSV2-HIG1-a.

(2) An Eco RI fragment of the human H-chain gene (HlGl) obtained in Example 3, with a size of about 21 Kbp, was inserted into the Eco RI site of vector pSV-2gpt developed by P. Berg to obtain two plasmids pSV2-HlGl-a and pSV2-HlGl-b having different orientations. The restriction endonuclease cleavage maps of these two plasmids are shown in FIG. 4.

E. coli MC 1000 strain was transformed with the hybrid DNA pSV2-HlGl-a and pSV2-HlGl-b, respectively. The resulting transformants were cultivated in a medium containing ampicilin. The plasmids were amplified with chloramphenicol, and then converted to protoplasts by lysozyme treatment. The resulting protoplasts were subjected to cell fusion with mouse myeloma cells ($2 \times 10^8$ cells) in the presence of 0.5 ml of 50% polyethylene glycol 4000 (PEG 4000) for 2 to 7 minutes. The fused cells were diluted in MEM medium and PEG was removed by centrifugation. After the cells were cultured in RPMI complete culture medium for half a day to one day, they were transferred to a selective medium containing 250 μg/ml of xanthine, 15 μg/ml of hypoxanthine and 6 μg/ml of mycophenolic acid. The medium was exchanged on two successive days, and after 2 weeks, colonies having resistance to mycophenolic acid were obtained.

The frequency of the resulting colonies is tabulated below.

| | Number of colonies | |
|---|---|---|
| | Cell line | |
| Vector | J558L | NS-1 |
| pSV2-H1G1 | 8/9 | 4/6 |

Nine or 6 wells of a plate having 24 wells were used, and $5 \times 10^6$ cells per well were inoculated. The number of wells which showed growth was determined, and defined as the number of colonies.

With regard to the above colonies, the human immunoglobulin H-chain was detected from the supernatant of the culture by the ELISA method (enzyme-linked immunosorbent assay). It was found that a human immunoglobulin H-chain was secreted in the supernatant with regard to psV2-H1G1 colonies for J558L. Then, cytoplasmic staining was carried out by the immunofluorescence technique. As a result, a human immunoglobulin H-chain could be detected in the cytoplasm in all of the colonies in which the human H-chain was secreted in the supernatant of the culture and in one colonies of pSV2-H1G1/J558L.

(3) Total RNA was extracted from a transformant obtained by inserting one copy of H1G1 into mouse myeloma NS-1 DNA, and northern hybridization was carried out using as a probe 1.9 Kb -Pst I fragment containing $C_{\gamma 1}$ gene, which is interposed between the 5'-terminal position [Pst I-(2)] and the 3'-terminal position [Pst I-(3)] of pTJ5 in FIG. 3. m-RNA of H1G1 was detected at 1.8 Kb, and its amount was about 50 to 100 times the amount of the original human lymphoma ARH77.

The colony was internally labelled with $^{35}S$ methionine, and the human H-chain was precipitated with Protein A-Sepharose 4B (a product of Pharmacia Fine Chemicals) using anti-human IgG. The precipitate was examined by SDS-polyacrylamide gel (SDS-PAGE) electrophoresis. It was found that a band assigned to a secretor-type H-chain and a band assigned to a membrane-type H-chain were obtained respectively at 54 Kilodalton and 68 Kilodalton, and both of the secretor-type and the membrane-type expressed in the cells.

The amount of secretor-type H-chain was 50 to 100 times that of the chain protein of ARH77.

EXAMPLE 11

Function of increasing expression of an enhancer and the 5'-flanking region containing a direct repeat sequence (promoter sequence)

The 2.3 Kb Eco RI-Sph I DNA fragment of a human immunoglobulin H-chain gene having a direct repeat sequence and a 5'-flanking region was joined at the Sph I site to the Sph I site of a human beta-globin gene [The Journal of Biological Chemistry, 258 (19), 11599–11609 (1983), Doncz, M., Schwart, E, Ballentine, M., and Surrey, S.], which exists upstream of the 5'-terminal of human beta-globin gene. By this joining, the orientation of transcription would become the same.

Likewise, the 1.4 Kb Aat II-Hpa I DNA flagment containing a human enhancer was joined at the Hpa I site to the Hpa I site of the human beta-globin gene, which site exists upstream of the 5'-terminal of beta-globin gene so as to obtain the same orientation of transcription.

Using vector pBR322, plasmids having hybrid DNAs joined as above were prepared, and E. coli MC 1000 strain was transformed with each of these plasmids by the RbCl method. The E. coli MC 1000 transformant containing the plasmid was subjected to protoplast fusion with mouse myeloma J558L to introduce the plasmid into the mouse myeloma J558L. The cells were grown in RPMI complete medium for 72 hours, and 300 micrograms of RNA was obtained from about $1 \times 10^7$ cells.

Twenty micrograms of the resulting RNA was subjected to northern hybridization using a Bam HI-Eco RI fragment of the human beta-globin containing Exon 2 and Exon 3 as a probe. A band was detected at 5S, and the expression of m-RNA ascribable to the human beta-globin gene was observed.

From the densities of the band, the intensities of expression were compared. It was found that whether the 5'-flanking region containing the direct repeat sequence was joined or the enhancer was joined, expression of the level of transcription was 5 to 10 times as large as that in a control where only the human beta-globin gene was used without hybridization.

What we claim is:

1. An enhancer DNA segment comprising a strand containing at least the following DNA units $E_1$, $E_2$, $E_3$, $E_7$, $E_5$ and $E_6$:

unit $E_1$: —AAAACAC— unit $E_2$: —TGGTTGTGAA— unit $E_3$: —GTGGTTTTG— unit $E_7$: —TGCAATTT— unit $E_5$: —GTGGCAGG— unit $E_6$: —GGCCCAGAT— wherein A represents deoxyadenosine 5'-phosphate, C represents deoxycyt,idine 5 -phosphate, G represents deoxyguanosine 5 phosphate and T represents deoxythymidine 5'-phosphate, in a sequence wherein $E_1$ is positioned on the side of the 5'-terminus to $E_2$ and wherein $E_3$ is positioned on the side of the 3'-terminus to $E_2$ and wherein $E_7$ is positioned on the side of the 3'-terminus to $E_3$ and wherein the unit $E_5$ is present on the side of the 5'-terminus to the unit $E_1$ and wherein the unit $E_6$ is present on the side of the 3'-terminus to the unit $E_3$ but on the side of the 5'-terminus to the unit $E_7$ and a complementary strand thereof,
   and wherein the total number of base pairs is not more than 150.

2. The enhancer DNA segment which comprises the following DNA unit $E_0$

TTGAGCGAAGCTGGAAGCAGATG

ATGAATTAGAGTCAAGATGGCTG

CATGGGGGTCTCCGGCACCCACA

GCAGGTGGCAGGAAGCAGGTCAC

CGCGAGAGTCTATTTTAGGAAGC

AAAAAAACACAATTGGTAAATTT

ATCACTTCTGGTTGTGAAGAGGT

GGTTTTGCCCAGGCCCAGATCTG

AAAGTGCTCTACTGAGCAAAACA

ACACCTGGACAATTTGCGTTTCT

AAAATAAGGCGAGGCTGACCGAA

ACTGAAAAGGCTTTTTTTAACTA

TCTGCAATTTCATTTCCAATCTT

AGCTTA and a complementary strand therefor.

3. The enhancer DNA segment of claim 2 wherein the following unit $E_t$

TCAACTGCTAGTTGG is directly bonded to the 3'-terminus of said unit $E_0$.

4. The enhancer DNA segment of claim 2 wherein the following unit $E_i$

TTATTTTTTTAATTAA is directly bonded to the 5'-terminus of said DNA unit $E_0$.

5. A gene fragment comprising (a) the enhancer DNA segment which comprises a strand containing at least the following DNA units $E_1$, $E_2$, $E_3$ and $E_7$:

unit $E_1$: —AAAACAC— unit $E_2$: —TGGTTGTGAA— unit $E_3$: —GTGGTTTTG— unit $E_7$: —TGCAATTT—, wherein A represents deoxyadenosine 5'-phosphate, C represents deoxycytidine 5'-phosphate, G represents deoxyguanosine 5'-phosphate and T represents deoxythymidine 5'-phosphate, in a sequence wherein $E_1$ is positioned on the side of the 5'-terminus to $E_2$ and wherein $E_3$ is positioned on the side of the 3'-terminus to $E_2$ and wherein $E_7$ is positioned on the side of the 3'-terminus to $E_3$ and a complementary strand thereof, and said segment having a total number of base pairs of not more than 300 and (b) a structural gene.

6. A gene fragment comprising (a) an enhancer DNA segment which comprises a strand containing at least the following DNA units $E_1$, $E_2$, $E_3$ and $E_7$:

unit $E_1$: —AAAACAC— unit $E_2$: —TGGTTGTGAA— unit $E_3$: —GTGGTTTTG— unit $E_7$: —TGCAATTT—, wherein A represents deoxyadenosine 5'-phosphate, C represents deoxycytidine 5'-phosphate, G represents deoxyguanosine 5'-phosphate and T represents deoxythymidine 5'-phosphate, in a sequence wherein $E_1$ is positioned on the side of the 5'-terminus to $E_2$ and wherein $E_3$ is positioned on the side of the 3'-terminus to $E_2$ and wherein $E_7$ is positioned on the side of the 3'-terminus to $E_3$ and a complementary strand thereof, and said segment having a total number of base pairs of not more than 300 and (b) a structural gene, wherein the structural gene is at least one human gene fragment which consists of: i) a human D gene composed of a strand represented by the following DNA sequence $D_0$

GGCCTCCTCCGGGGGGCTGGAA

CGACGTGG wherein A, C, G and T are as defined hereinabove, and a complementary strand thereof, ii) a human V gene composed of a strand represented by the following DNA sequence $V_o$

CAGGTGCAGCTACACCAGTGGGG

CGCAGGACTGGTGAAGCCTTCGG

AGACCCTGTCCCTCACCTGCGCT

GTCTTTGGTGGGTCCTTCAGTGG

TTACTACTGGAGCTGGATCCGCC

AGCCCCCAGGAAGGGGACTGGAG

TGGATTGGAGAAATCAATCATAG

TGGAAGCACCAATTACAAAACGT

CCCTCAAGAGTCGAGTCACCATA

TCTTTAGACACGTCCAAGAACCT

GTTCTCCCTGAAGCTGAGCTCTG

TGACCGCCGCGGACACGGCTGTG

TATTACTGTGCGAGG wherein A, C, G and T are as defined hereinabove, and a complementary strand thereof, and iii) a human J gene composed of a strand represented by the following DNA sequence $J_o$

ACTACTACTATGGTATGGACGTC

TGGGGCCAAGGGACCACGGTCAC

CGTCTCCTCA wherein A, C, G and T are as defined hereinabove, and a complementary strand thereof and wherein the human V gene, the human D gene and the human J gene are bonded to one another, the human V gene being positioned on the side of the 5'-terminus to the human D gene and the human J gene being positioned on the side of the 3-terminus to the human D gene.

7. The gene fragment of claim 6 wherein the human D gene codes a polypeptide chain represented by the following amino acid sequence $AD_o$ GlyLeuLeuArgGlyGlyTrpAsnAspVal wherein Gly, Leu, Arg, Trp, Asn, Asp and Val respectively represent glycine, leucine, arginine, tryptophan, asparagine, aspartic acid and valine.

8. The gene fragment of claim 6 wherein the human V gene codes a polypeptide chain represented by the following amino acid sequence $AV_o$ GlnValGlnLeuGlnGlnTrpGlyAlaGly LeuValLysProSerGluThrLeuSerLeu ThrCysAlaValPheGlyGlySerPheSer GlyTyrTyrTrpSerTrpIleArgGlnPro ProGlyArgGlyLeuGluTrpIleGlyGlu IleAsnHisSerGlySerThrAsnTyrLys ThrSerLeuLysSerArgValThrIleSer LeuAspThrSerLysAsnLeuPheSerLeu LysLeuSerSerValThrAlaAlaAspThr AlaValTyrTyrCysAlaArg wherein Gly, Leu, Arg, Trp, Asn, Asp and Val are defined, and Ala, Lys, His, Ile, Phe, Ser, Try, Thr, Cys, Pro, Met, Glu and Gln respectively represent alanine, lysine, histidine, isoleucine, phenylalnine, serine, tyrosine, threonine, cystine, proline, methionine, glutamic acid and gluttamine.

9. The gene fragment of claim 6 wherein the human J gene codes a polypeptide chain represented by the following amino acid sequence $AJ_o$ AspTyrTyrTyrGlyMetAspValTrpGly GlnGlyThrThrValThrValSerSer wherein Asp, Try, Gly, Met, Asp, Val, Trp, Gly, Gln, Thr, Val and Ser are as defined.

10. The gene fragment of claim 5 wherein the structural gene is a human beta-globulin gene.

11. The gene fragment of claim 5 wherein the enhancer DNA segment (a) is separated from the structural gene (b) by a distance of up to about 5 Kbp.

12. The gene fragment of claim 5 wherein the structural gene (b) is situated on the side of 5'-terminal base of the enhancer DNA segment (a).

13. A human D m-RNA comprising a strand represented by the following RNA sequence $RD_o$ ggccuccuccggggggcuggaa cgacgugg wherein, a represents adenosine 5'-phosphate, c represents cytidine 5'-phosphate, g represents guanosine 5'-phosphate and u represents uridine 5'-phosphate.

14. A human V m-RNA comprising a strand represented by the following RNA sequence $RV_o$ caggugcagcuacagcagugggg cgcaggacuggugaagccuucgg agacccugucccucaccugcgcu gucuuuggugguccuucagugg uuacuacuggagcuggauccgcc agcccccaggaaggggacuggag uggauuggagaaaucaaucauag uggaagcaccaauuacaaaacgu cccucaagagucgagucaccaua ucuuuagacacguccaagaaccu guucucccugaagcugagcucug ugaccgccgcggacacggcugug uauuacugugcgagg wherein a, c, g and u are as defined hereinabove.

15. A human V and D m-RNA fragment comprising the human D m-RNA comprising a strand represented by said RNA base sequence $RD_o$ comprising a strand represented by the following RNA sequence $RD_o$ ggccuccuccggggggcuggaa cgacgugg wherein a represents adenosine 5'-phosphate,, c represents cytidine 5'-phosphate, g represents guanosine 5'-phosphate and u represents uridine 5'-phosphate and the human V m-RNA comprising a strand represented by said RNA base sequence $RV_o$;

caggugcagcuacagcagugggg cgcaggacuggugaagccuucgg agacccugucccucaccugcgcu gucuuuggugguccuucagugg uuacuacuggagcuggauccgcc agcccccaggaaggggacuggag uggauuggagaaaucaaucauag uggaagcaccaauuacaaaacgu cccucaagagucgagucaccaua ucuuuagacacguccaagaaccu guucucccugaagcugagcucug ugaccgccgcggacacggcugug uauuacugugcgagg wherein a, c, g and u are as defined hereinabove, the human V m-RNA being located on the side of the 5'-terminal base of the human D m-RNA.

16. A human V, D and J m-RNA fragment comprising the human D m-RNA comprising a strand represented by said RNA base sequence $RD_o$ comprising a strand represented by the following RNA sequence $RD_o$ ggccuccuccggggggcuggaa cgacgugg wherein a represents adenosine 5'-phosphate, c represents cytidine 5'-phosphate, g represents guanosine 5'-phosphate and u represents uridine 5'-phosphate.

the human V m-RNA comprising a strand represented by the following RNA base sequence $RV_o$:

caggugcagcuacagcagugggg cgcaggacuggugaagccuucgg agacccuguccccucaccugcgcu gucuuuggugggguccuucagugg uuacuacuggagcuggauccgcc agcccccaggaaggggacuggag uggauuggagaaaucaaucauag uggaagcaccaauuacaaaacgu cccucaagagucgagucaccaua ucuuuagacacguccaagaaccu guucucccugaagcugagcucug ugaccgccgcggacacggcugug uauuacugugcgagg and a human J m-RNA comprising a strand represented by the following RNA base sequence $RJ_o$:

acuacuacuaugguauggacguc uggggccaagggaccacggucac cgucuccuca wherein a, c, g and u are defined, as above, the human D m-RNA being present, between the 3'-terminal base of the human V m-RNA and the 5'-terminal base of the human J m-RNA.

17. The enhancer DNA segment of claim 1 which further comprises the following DNA unit $E_4$:

unit $E_4$: —TGATGAAT— wherein A, G and T are as defined above, wherein $E_4$ is positioned on the side of the 5'-terminus to $E_1$ and a complementary strand thereof.

18. A human D gene fragment comprising a strand represented by the following DNA sequence $D_0$:

GGCCTCCTCCGGGGGGGCTGGAA

CGACGTGG wherein A represents deoxyadenosine 5'-phosphate, C represents deoxycytidine 5'-phosphate, G represents deoxyguanosine 5'-phosphate and T represents deoxythymidine 5'-phosphate, and a complementary strand thereof.

19. A human V gene fragment comprising a strand represented by the following DNA sequence $V_0$:

CAGGTGCAGCTACACCAGTGGGG

CGCAGGACTGGTGAAGCCTTCGG

AGACCCTGTCCCTCACCTGCGCT

GTCTTTGGTGGGTCCTTCAGTGG

TTACTACTGGAGCTGGATCCGCC

AGCCCCCAGGAAGGGGACTGGAG

TGGATTGGAGAAATCAATCATAG

TGGAAGCACCAATTACAAAACGT

CCCTCAAGAGTCGAGTCACCATA

TCTTTAGACACGTCCAAGAACCT

GTTCTCCCTGAAGCTGAGCTCTG

TGACCGCCGCGGACACGGCTGTG

TATTACTGTGCGAGG wherein A represents deoxyadenosine 5'-phosphate, C represents deoxycytidine 5'-phosphate, G represents deoxyguanosine 5'-phosphate and T represents deoxythymidine 5'-phosphate, and a complementary strand thereof.

20. A human V and D gene fragment comprising a human V gene composed of a strand represented by the following DNA sequence $V_0$:

CAGGTGCAGCTACACCAGTGGGG

CGCAGGACTGGTGAAGCCTTCGG

AGACCCTGTCCCTCACCTGCGCT

GTCTTTGGTGGGTCCTTCAGTGG

TTACTACTGGAGCTGGATCCGCC

AGCCCCCAGGAAGGGGACTGGAG

TGGATTGGAGAAATCAATCATAG

TGGAAGCACCAATTACAAAACGT

CCCTCAAGAGTCGAGTCACCATA

TCTTTAGACACGTCCAAGAACCT

GTTCTCCCTGAAGCTGAGCTCTG

TGACCGCCGCGGACACGGCTGTG

TATTACTGTGCGAGG wherein A represents deoxyadenosine 5'-phosphate, C represents deoxycytidine 5'-phosphate, G represents deoxyguanosine 5'-phosphate and T represents deoxythymidine 5'-phosphate, and a complementary strand thereof and a human D gene composed of a strand represented by the following DNA sequence $D_0$:

GGCCTCCTCCGGGGGGGCTGGAA

CGACGTGG wherein A, C, G and T are as defined hereinabove, and a complementary strand thereof, the human V gene being positioned on the side of the 5'-terminal base of the human D gene.

21. A human V, D and J gene fragment comprising a human V gene composed of a strand represented by the following DNA sequence $V_0$:

CAGGTGCAGCTACACCAGTGGGG

CGCAGGACTGGTGAAGCCTTCGG

AGACCCTGTCCCTCACCTGCGCT

-continued

GTCTTTGGTGGGTCCTTCAGTGG

TTACTACTGGAGCTGGATCCGCC

AGCCCCCAGGAAGGGGACTGGAG

TGGATTGGAGAAATCAATCATAG

TGGAAGCACCAATTACAAAACGT

CCCTCAAGAGTCGAGTCACCATA

TCTTTAGACACGTCCAAGAACCT

GTTCTCCCTGAAGCTGAGCTCTG

TGACCGCCGCGGACACGGCTGTG

TATTACTGTGCGAGG wherein A represents deoxyadenosine 5'-phosphate, C represents deoxycytidine 5'-phosphate, G represents deoxyguanosine 5'-phosphate and T represents deoxythymidine 5'-phosphate, and a complementary strand thereof and a human D gene composed of a strand represented by the following DNA sequence $D_0$:

GGCCTCCTCCGGGGGGGCTGGAA

CGACGTGG wherein A, C, G and T are as defined hereinabove, and a complementary strand thereof and a human J gene composed of a strand represented by the following DNA sequence $J_0$:

ACTACTACTATGGTATGGACGTC

TGGGGCCAAGGGACCACGGTCAC

CGTCTCCTCA wherein A, C, G and T are as defined, and a complementary strand, thereof, the human D gene being positioned between the 3'-terminal base of the human V gene and the 5'-terminal base of the human J gene.

* * * * *